(12) United States Patent
Wittnebel et al.

(10) Patent No.: US 10,980,672 B2
(45) Date of Patent: Apr. 20, 2021

(54) FEMTOSECOND LASER OPHTHALMIC SURGERY DOCKING CONE IMAGE PROCESSING AND PRESENTATION

(71) Applicant: Alcon Inc., Fribourg (CH)

(72) Inventors: Michael Wittnebel, Hirschaid (DE); Mario Abraham, Burgthann (DE); Stefan Schmid, Neuendettelsau (DE); Martin Starigk, Nuremberg (DE)

(73) Assignee: Alcon Inc., Fribourg (CH)

( * ) Notice: Subject to any disclaimer, the term of this patent is extended or adjusted under 35 U.S.C. 154(b) by 138 days.

(21) Appl. No.: 16/098,007

(22) PCT Filed: May 2, 2016

(86) PCT No.: PCT/IB2016/052493
§ 371 (c)(1),
(2) Date: Oct. 31, 2018

(87) PCT Pub. No.: WO2017/191486
PCT Pub. Date: Nov. 9, 2017

(65) Prior Publication Data
US 2019/0142633 A1    May 16, 2019

(51) Int. Cl.
*A61F 9/00* (2006.01)
*A61F 9/009* (2006.01)
*A61F 9/008* (2006.01)

(52) U.S. Cl.
CPC .......... *A61F 9/009* (2013.01); *A61F 9/00804* (2013.01); *A61F 2009/00872* (2013.01); *A61F 2009/00887* (2013.01)

(58) Field of Classification Search
CPC .................. A61F 9/009; A61F 9/00804; A61F 2009/00872; A61F 2009/00887
USPC .......................................................... 606/4
See application file for complete search history.

(56) References Cited

U.S. PATENT DOCUMENTS

| | | | |
|---|---|---|---|
| 2004/0260275 A1* | 12/2004 | Liang .................... | A61F 9/008 606/5 |
| 2007/0173791 A1 | 7/2007 | Raksi | |
| 2009/0247997 A1* | 10/2009 | Watanabe ........... | A61F 9/00829 606/4 |
| 2009/0247998 A1* | 10/2009 | Watanabe ............... | A61F 9/008 606/5 |

(Continued)

FOREIGN PATENT DOCUMENTS

| | | | | |
|---|---|---|---|---|
| EP | 2913036 A1 * | 9/2015 | ......... | A61F 9/00825 |
| EP | 2913036 A1 | 9/2015 | | |

*Primary Examiner* — Carl H Layno
*Assistant Examiner* — Michael J Lau

(57) ABSTRACT

The present disclosure provides a system for femtosecond ophthalmic surgery in which the position of a suction cone in the z direction is measured via the measuring device to generate data that is processed and used to create a pictorial representation, a histogram, or other graph based on the data. The pictorial representation may include at least one threshold marker. The disclosure further provides a method of performing docking in femtosecond laser ophthalmic surgery including measuring the position of a suction cone with a measuring device, and transmitting data regarding the position to a processor which processes the data and uses it to create a pictorial representation, histogram, or other graph that is presented on a display.

15 Claims, 8 Drawing Sheets

(56) References Cited

U.S. PATENT DOCUMENTS

| | | | |
|---|---|---|---|
| 2011/0202044 A1* | 8/2011 | Goldshleger | A61B 3/102 |
| | | | 606/4 |
| 2013/0102922 A1* | 4/2013 | Gooding | A61F 9/009 |
| | | | 600/558 |
| 2013/0338649 A1* | 12/2013 | Hanebuchi | A61F 9/0084 |
| | | | 606/4 |
| 2014/0114296 A1* | 4/2014 | Woodley | A61B 5/4836 |
| | | | 606/6 |
| 2014/0114297 A1* | 4/2014 | Woodley | A61B 5/0036 |
| | | | 606/6 |
| 2014/0128731 A1 | 5/2014 | Gonzalez et al. | |
| 2014/0128852 A1* | 5/2014 | Gooding | A61F 9/008 |
| | | | 606/4 |
| 2014/0276678 A1* | 9/2014 | Berry | A61F 9/009 |
| | | | 606/5 |
| 2015/0190278 A1* | 7/2015 | Gooding | A61F 9/009 |
| | | | 606/4 |
| 2015/0335479 A1* | 11/2015 | Shibata | A61F 9/009 |
| | | | 606/5 |
| 2020/0246183 A1* | 8/2020 | Wittnebel | A61F 9/008 |

\* cited by examiner

POSITION OF CONE IN z DIRECTION

TIME

FEMTOSECOND LASER OPHTHALMIC SURGERY DOCKING CONE IMAGE PROCESSING AND PRESENTATION

CROSS REFERENCE TO RELATED APPLICATIONS

This application is a section 371 national stage phase of International Application No. PCT/IB2016/52493, filed 2 May 2016, titled "FEMTOSECOND LASER OPHTHALMIC SURGERY DOCKING CONE IMAGE PROCESSING AND PRESENTATION," which is hereby incorporated by reference in its entirety.

TECHNICAL FIELD

The present disclosure relates to ophthalmic surgery and surgical equipment, and more specifically, to systems for and methods of processing and presenting an image during docking on an eye in femtosecond laser ophthalmic surgery.

DESCRIPTION OF THE RELATED ART

In ophthalmology, ophthalmic surgery is performed on the eye and accessory visual structures to save and improve the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make a tremendous difference in the patient's vision after the surgery.

One type of ophthalmic surgery, refractive eye surgery, is used to correct a variety of vision problems. One common such refractive surgery is known as LASIK (laser-assisted in situ keratomileusis) and is used to correct myopia and hyperopia, astigmatism, or more complex refractive errors. Other ophthalmic surgeries may correct corneal defects or other problems. For instance, phototherapeutic keratectomy (PTK) may be used to remove diseased corneal tissue or corneal irregularities either alone or in combination with LASIK. Another common ophthalmic surgery is the removal of cataracts.

During LASIK, PTK, cataract surgery, and other ophthalmic surgeries, corrective procedures are commonly performed on interior parts of the eye, such as the corneal stroma or the lens, rather than on the eye surface. This practice tends to improve surgical outcomes by allowing the corrective procedure to be targeted to the most effective part of the eye, by keeping the outer, protective parts of the cornea largely intact, and for other reasons.

The interior part of the eye may be accessed in a variety of manners, but frequently access involves cutting a flap in the cornea or otherwise cutting the cornea. Corneal cutting is often performed by a femtosecond laser that creates focused ultrashort pulses, eliminating collateral damage of surrounding tissues associated with slower lasers and complications associated with mechanical cutting instruments, such as blades. Femtosecond lasers can therefore be used to dissect tissue on a microscopic level.

Femtosecond laser ophthalmic surgery typically includes docking, imaging, analysis, and laser treatment.

During docking, a patient's eye is docked to a suction cone in order to provide pressure to flatten the patient's cornea (known as applanation) and hold it in position for the laser treatment. A curved cone, which does not flatten the cornea, may also be used for the docking process. Docking is a sensitive process, and proper placement of the suction cone is important for successful femtosecond laser ophthalmic surgery. However, correct placement of the suction cone is currently typically guided through visual inspection by the user, relying on experience and perception.

SUMMARY

The present disclosure provides a system for femtosecond laser ophthalmic surgery. The system includes a suction cone, a control device operable to move the suction cone up and down in a z direction, a measuring device operable to measure the position of the suction cone in the z direction and generate data relating to the measured position, a processor operable to process data relating to the measured position of the suction cone to create a pictorial representation, histogram, or other graph based on the position of the suction cone in the z direction, and a display operable to receive the pictorial representation, histogram, or other graph when transmitted from the processor and to present the pictorial representation, histogram, or other graph during femtosecond laser ophthalmic surgery.

In additional embodiments, which may be combined with one another unless clearly exclusive: the measuring device includes a light barrier, a switch, a distance-measuring device, or a combination thereof; the display includes a screen, a head-up display, or a combination thereof, the processor is operable to create and the display is operable to present the pictorial representation, histogram, or other graph in real time; the processor is operable to process information data relating to the measured position to create at least two of a pictorial representation, a histogram, or other graph based on the position of the suction cone in the z direction and the display is operable to display at least two of the pictorial representation, histogram, or other graph simultaneously; the display presents a pictorial representation including a threshold marker corresponding to at least one threshold position of the suction cone in the z direction; the at least one threshold position includes a rest threshold position, a low contact threshold position, a high contact threshold position, an ideal work area threshold position, and a z stop limit threshold position; the display presents a pictorial representation including threshold markers corresponding to all of the threshold positions; the display presents a warning indicator when the suction cone reaches the z stop threshold position; the processor is further operable to determine when the suction cone reaches a z stop threshold position and to stop further upward movement of the suction cone in the z direction when the suction cone reaches the z stop threshold position; the processor is further operable to create and the display is further operable to present a pictorial representation of applanation of the eye; the system is further operable to record the measured positions of the suction cone over time and the processor is further operable to create and the display is further operable to present a histogram of the measured positions of the suction cone over time; and the processor is further operable to create a pictorial representation, histogram, or other graph depicting a load resting on the eye as a function of the measured position of the suction cone.

The present disclosure further provides a method of docking a suction cone in femtosecond laser ophthalmic surgery. The method includes measuring the position of the suction cone in the z direction using a measuring device, generating data relating to the measured position of the suction cone using the measuring device, processing the data relating to the measured position of the suction cone with a processor to create a pictorial representation, histogram, or other graph of the position of the suction cone in the z direction, and transmitting the pictorial representation, histogram, or other graph from the processor to a display that presents the pictorial representation, histogram, or other graph.

In additional embodiments, which may be combined with one another unless clearly exclusive: the position of the suction cone in the z direction may be measured at at least one threshold position of the suction cone in the z direction; the at least one threshold position includes a rest threshold position, a low contact threshold position, a high contact threshold position, an ideal work area threshold position, and a z stop limit threshold position; the display presents a warning indicator when the suction cone reaches the z stop threshold position; upward movement of the suction cone in the z direction is stopped when the suction cone has reached the z stop threshold position; the suction cone changes position over time, the processor further processes data relating to the measured position of the suction cone over time to produce a histogram of the measured position of the suction cone over time, and the display displays the histogram; and the processor uses data relating to the measured position of the suction cone to determine the load of the suction cone resting on the eye and to create a graph depicting this load, which is transmitted to and presented by the display.

The above systems may be used with the above methods and vice versa. In addition, any system described herein may be used with any method described herein and vice versa.

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which.

DETAILED DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments.

The present disclosure provides systems and methods for docking a suction cone on an eye in a femtosecond laser ophthalmic surgery. The system measures the position of the suction cone during docking, processes data relating to the measured position, and presents a pictorial representation or a histogram based on the measured position, both of which may be accompanied by other representations, such as other graphs or a pictorial representation of applanation of the cornea during docking.

In the present disclosure, "lower," "down" and "downwards" in the z direction refer to movement or a position closer to the patient's eye. "Higher," "up" and "upwards" in the z direction refer to movement or a position further away from the patient's eye.

Figure 1:
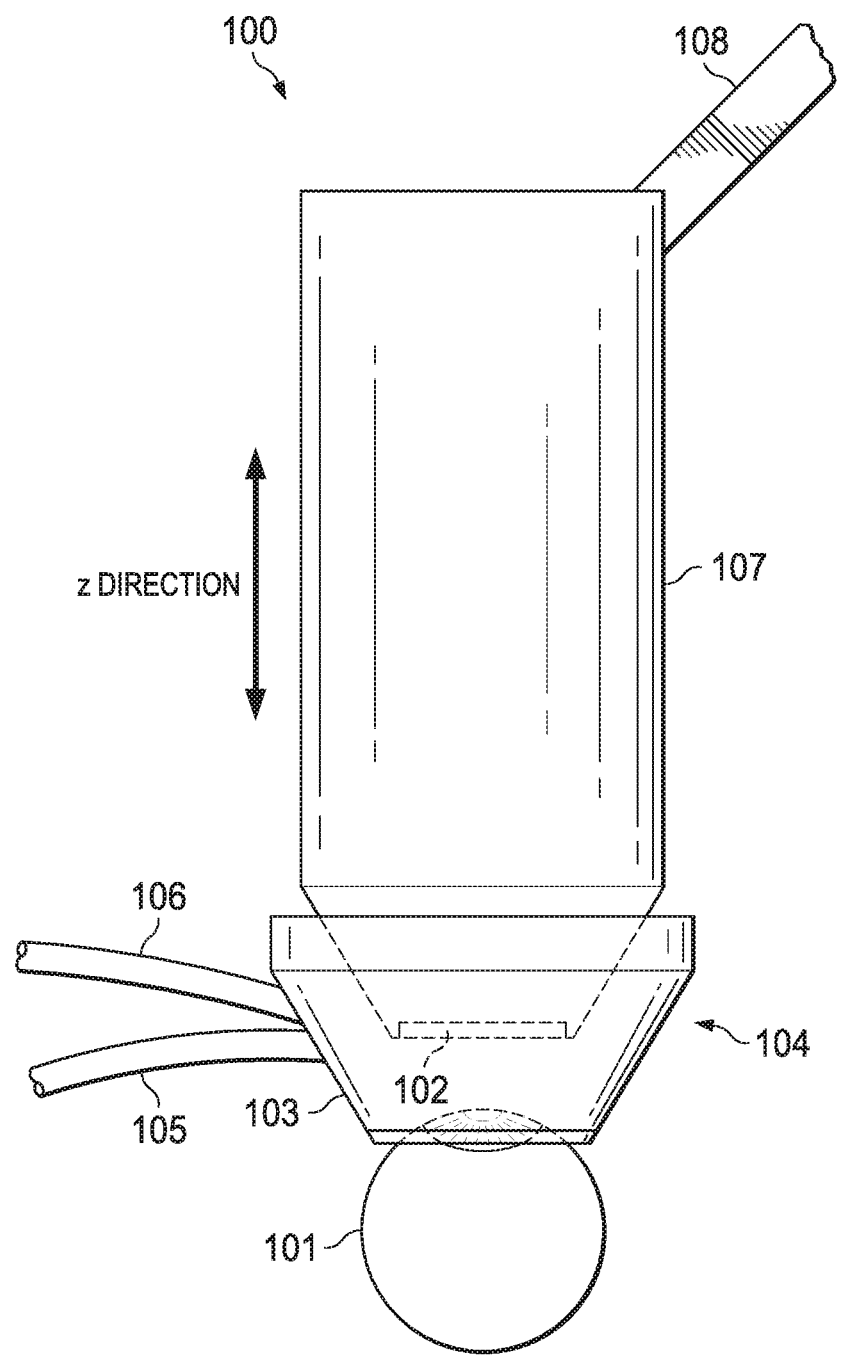
FIG. 1 is a schematic representation of a docking apparatus for femtosecond laser ophthalmic surgery.

FIG. 1 is a schematic representation of a docking apparatus 100 for femtosecond laser ophthalmic surgery. As shown, a typical docking apparatus 100 includes a suction ring 103 which is suctioned to a patient's eye 101, where a patient interface 104 fits within the suction ring 103. A series of two vacuums, first vacuum 105 and second vacuum 106 are attached to the suction ring and are used to provide suction to the patient's eye 101 at appropriate times.

During docking, the suction ring 103 is suctioned to the patient's eye 101 so that the suction ring is in contact with eye 101. Once the suction ring 103 has been properly positioned on the eye 101, first vacuum 105 is turned on to provide initial suction. The docking apparatus 100 further includes a suction cone 107 that fits into the suction ring 103. The suction cone includes a flat glass plate 102. The suction cone 107 may be lowered in the z direction by a control device 108 into the patient interface 104 within the suction ring 103, until the flat glass plate 102 makes contact with the eye 101. Alternatively, the suction cone 107 may remain stationery, while a patient's eye 101 is moved upwards towards the suction cone 107. This can be done, for example, by moving the patient upwards towards the suction cone 107. Once the glass plate 102 of the suction cone 107 makes contact with the eye 101, the suction cone 107 may be moved upwards in the z direction along with the eye 101 to provide different levels of contact with the patient's eye 101 until suction cone 107 reaches a threshold point in the z direction. After this threshold point is reached, second vacuum 106 is switched on and the suction cone 107 becomes firmly attached to the eye 101 by suctioning to the suction ring 103. This firm attachment to the eye 101 provides enough pressure to flatten the cornea of the patient's eye 101 because all or part of the cornea is within suction ring 103, a process which is known as applanation of the cornea. Once applanation occurs, docking is complete.

Proper placement of the suction cone during docking is important for successful ophthalmic surgery. However, in prior systems, the user was forced to rely on experience and perception to dock the suction cone properly, which makes it more difficult to attain proper placement and results in more placement errors. The present disclosure provides a system for femtosecond laser ophthalmic surgery in which the system contains a docking apparatus, such as that described above, and a measuring device to measure the position of the suction cone in the z direction during docking. The measuring device may include or be connected to a processor that uses the measured position to create a pictorial representation, histogram, or other graph of the position of the suction cone in the z direction or in relation to the cornea or another reference point on the eye, or of data relating to the measured position, such as the load of the suction cone on the eye or applanation of the cornea. One or more of these pictorial representations, histograms, or other graphs may be presented in real time during the femtosecond laser ophthalmic surgery. In addition, a single image or display may include more than one of these items. For instance, a single image may include both a pictorial representation and a histogram.

Figure 2:
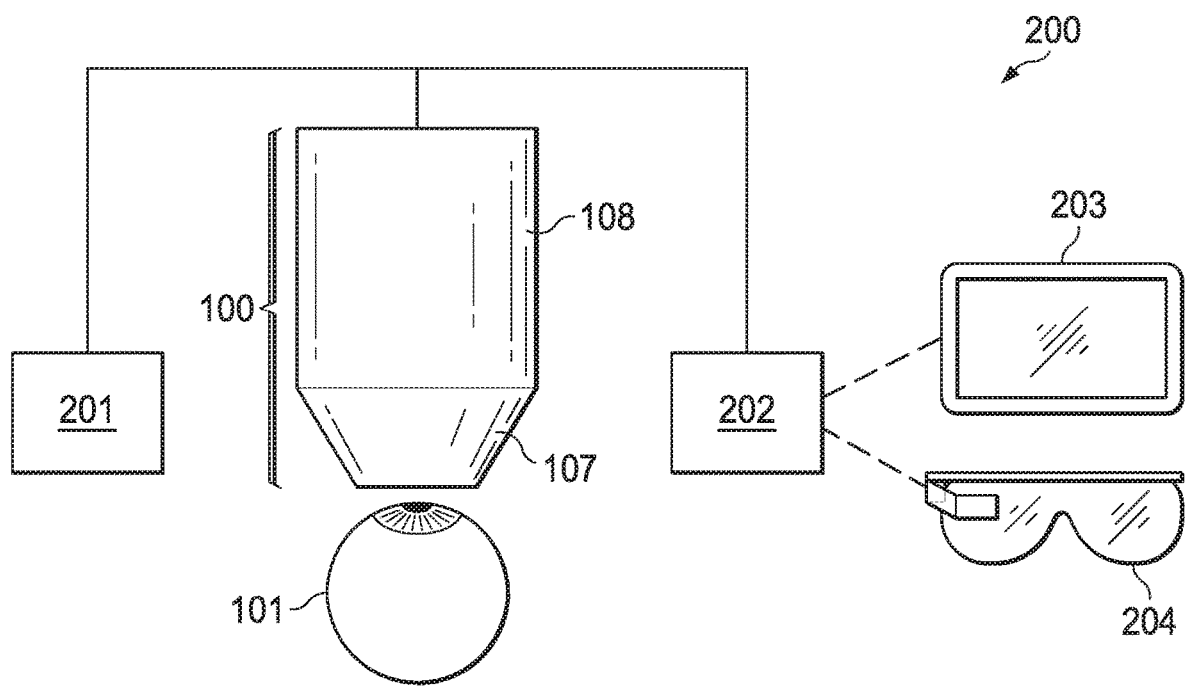
FIG. 2 is a schematic representation of elements of a system for femtosecond laser ophthalmic surgery including a docking apparatus such as that of FIG. 1.

Referring now to FIG. 2, a schematic representation of elements of a system for femtosecond laser ophthalmic surgery 200 including a docking apparatus 100, such as that of FIG. 1, is provided. Such a system may be used to measure the position of suction cone 107 in the z direction and it may use the measured position to present a pictorial representation, histogram, or other graph based on the measured position. As shown, the disclosed docking apparatus includes a suction cone 107; a control device 108 that is used to move the suction cone 107 up and down in the z direction; a measuring device 201 which measures the position of the suction cone 107; a processor 202 or equivalent programmed processing device that is included in or connected to the measuring device 201 and which processes data relating to the measured positions to create a pictorial representation, a histogram, or other graph of or based on the position of the suction cone 107 in the z direction, and which transmits a pictorial representation, histogram, or other graph to a display. The display may be in the form of a screen 203 or a head-up display 204. The system may present the pictorial representation, histogram, or other graph of or based on the position of the suction cone 107 in the z direction in real time to users so that they may adjust the position of the suction cone 107 accordingly using the control device 108. Real time may mean in less than half a second, in less than one second, or otherwise in less than the normal reaction time of a user of control device 108 based upon visual information.

Measuring device 201 may include lights barriers, switches, and distance measuring devices to measure the position of the suction cone 107 in the z direction. By way of non-limiting example, the distance measuring device may have a high resolution, as the overall acceptable moveable distance of suction cone 107 in the z direction is on the order of millimeters or centimeters. By way of non-limiting example, the light barriers and switches may only be able to measure or to otherwise react to the suction cone position at discrete positions. Measuring device 201 may also measure the position of the eye, the cornea, another reference point in the eye, or even an external reference point. Processor 202 may then use the measured position or positions to create a pictorial representation of the position of the suction cone 107 in the z direction as compared to the eye 101, or to perform calculations or other processing functions resulting in a histogram or other graph.

Figure 3A:
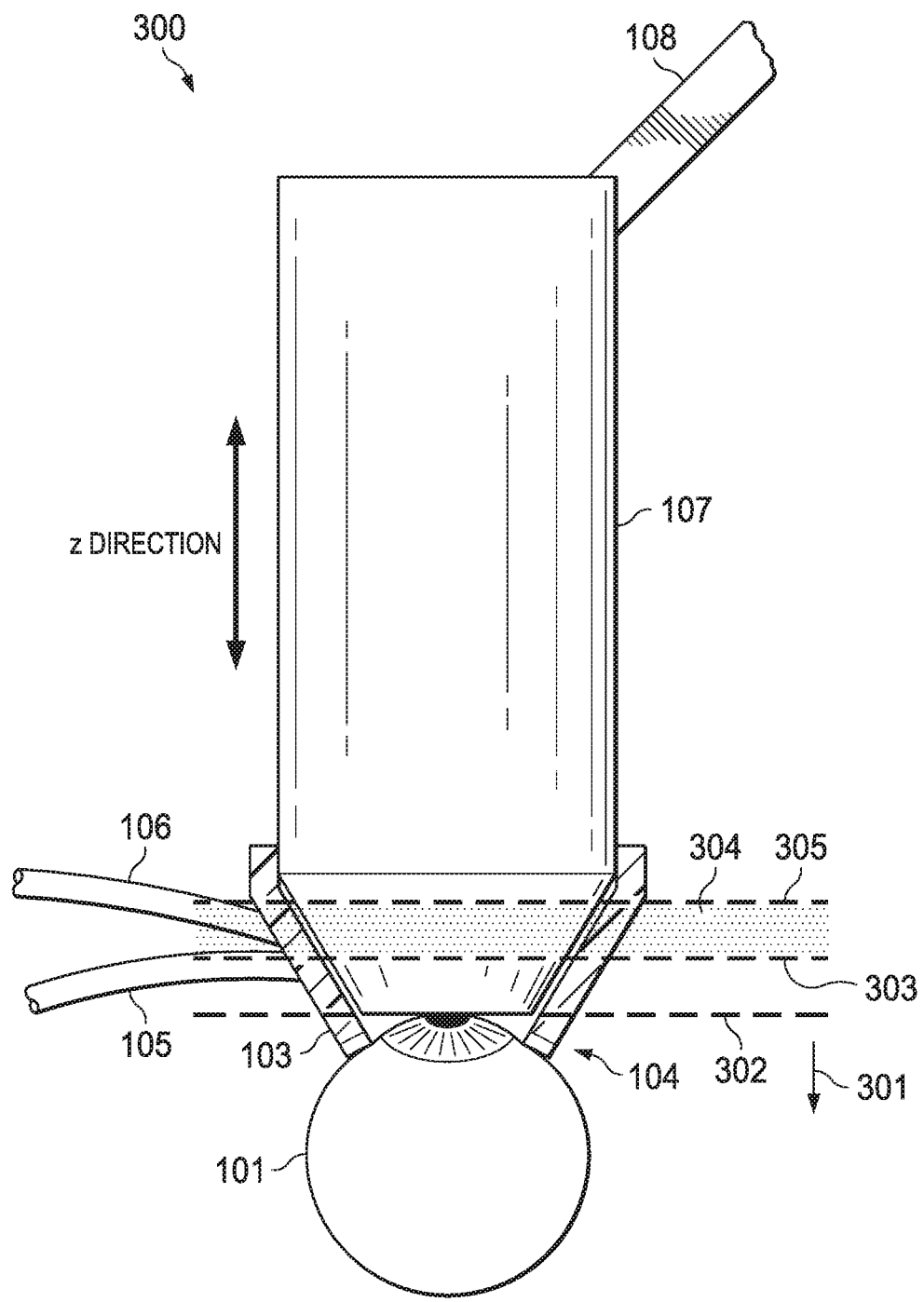
FIG. 3A is a schematic representation of a suction cone during docking on an eye in femtosecond laser ophthalmic surgery.
Figure 3B:
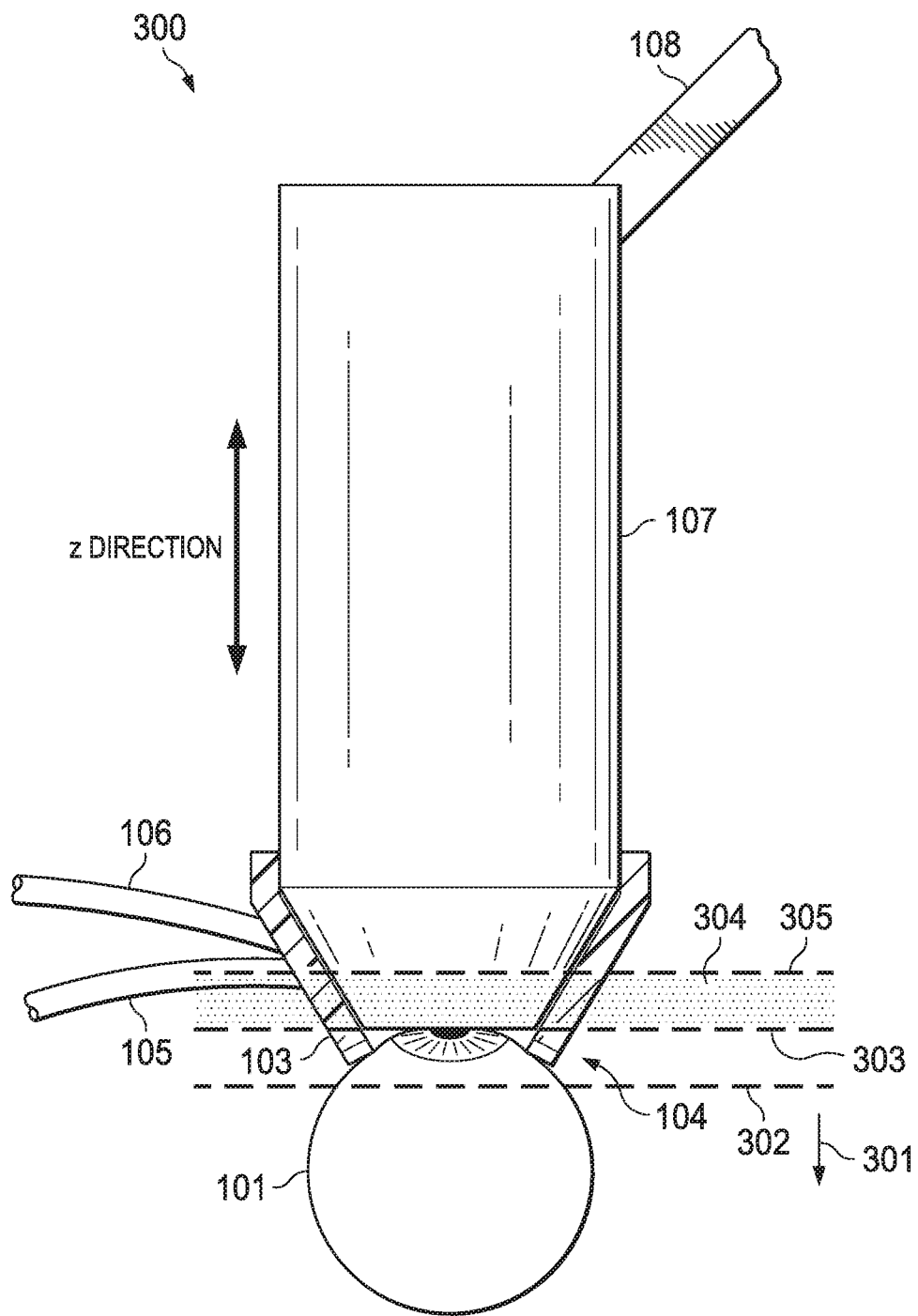
FIG. 3B is a schematic representation of the suction cone of FIG. 3A moved in the z direction with respect to FIG. 3A during docking on an eye in femtosecond laser ophthalmic surgery.
Figure 3C:
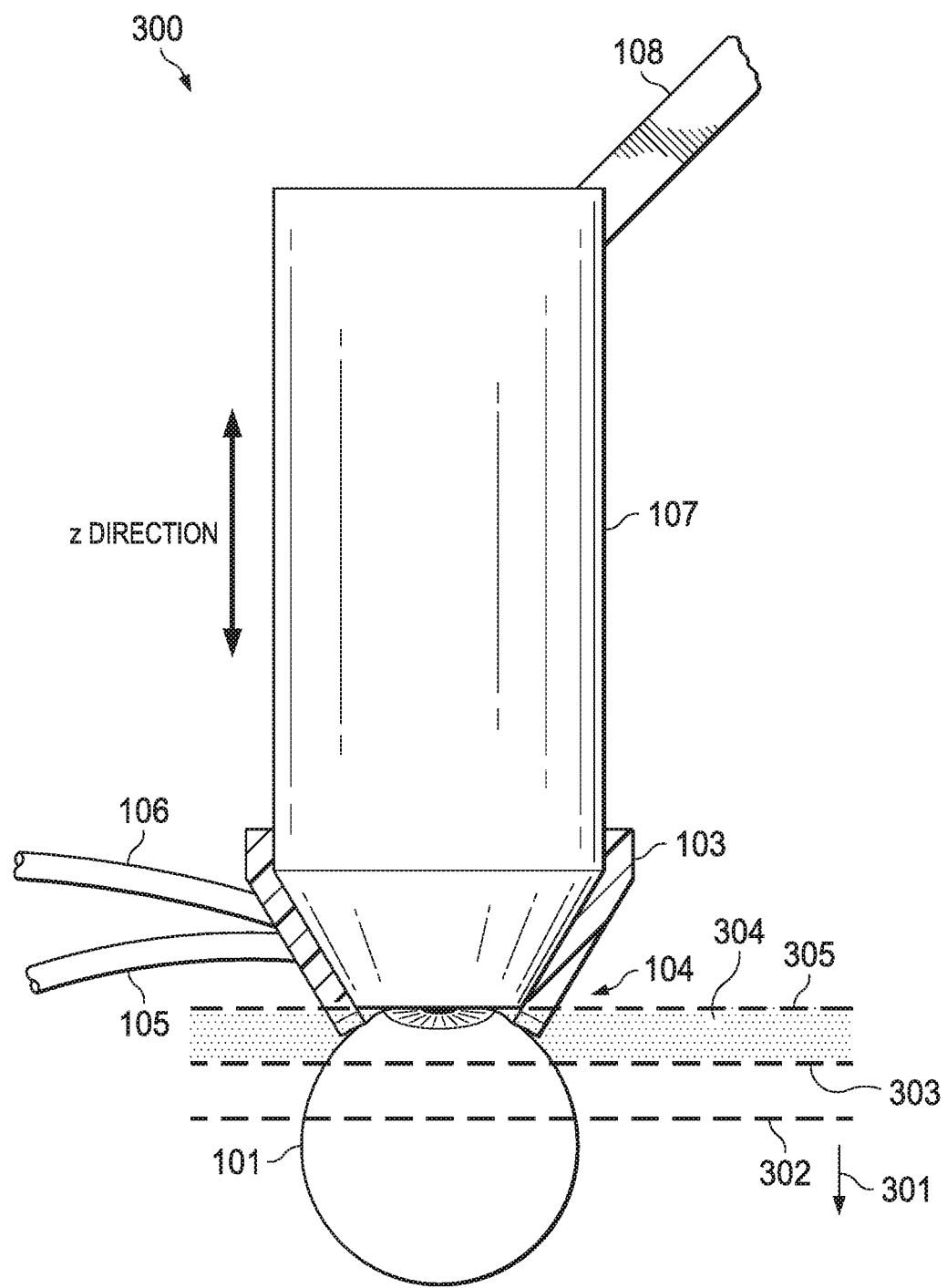
FIG. 3C is a schematic representation of the suction cone of FIG. 3B moved in the z direction with respect to FIG. 3B during docking on an eye in femtosecond laser ophthalmic surgery.

FIGS. 3A, 3B and 3C provide a schematic representation 300 of the movement of suction cone 107 in the z direction during docking on an eye 101 from a position 301 through at least some of a series of positions 302, 303, 304 and 305. In FIG. 3A, suction cone 107 is at position 302. In FIG. 3B, suction cone 107 has moved upward in the z direction to position 303. In FIG. 3C, suction cone 107 has moved upward in the z direction to position 305. The A portion of the patient's eye 101 moves upward in the z direction as well.

Referring to FIGS. 1, 2, and 3, when the suction cone 107 is first lowered into the suction ring 103 it is moved to rest position 301, where it is in contact with the eye 101. Once the suction cone 107 is at rest position 301, in contact with the eye 101, the position of the suction cone in the z direction may be measured by measuring device 201, which transmits the measured position in the z direction to processor 202, which then uses data relating to the measured position in the z direction to create a pictorial representation of the suction cone 107's position in the z direction that is presented on the display 203/204 for a user, as described further with reference to FIG. 4.

Next, the suction cone 107 is typically moved upward in the z direction, together with the patient's eye 101. There are a number of threshold positions that the suction cone 107 may reach when moving upwards in the z direction. Surgical system 200 may measure when each threshold position is reached and present related information, such as a threshold marker on the pictorial representation 300. The presentation may be in real time.

Specifically, as the suction cone 107 moves upwards, together with the eye, it reaches position 302, where contact with the eye 101 is considered low. When this position is measured via the measuring device 201, the display 203/204 will show that the suction cone 107 is in a low contact position with the eye 101, or "EC Low." A schematic representation of the suction cone 107 at this threshold position is shown in FIG. 3A.

Suction cone 107 then continues to travel upwards in the z direction until the measuring device 201 measures that the suction cone 107 has reached a position 303 of high contact with the eye, or "EC High" 303, this is also presented. A schematic representation of the suction cone 107 at this threshold position is shown in FIG. 3B. The second vacuum 106, switches on, either automatically or because the user activates it, and the suction cone 107 becomes firmly attached to the eye 101 by suctioning to the suction ring 103, which has already been suctioned to the eye 101 by the suction from the first vacuum 105. Once the suction cone 107 reaches position 303, and second vacuum 106 is initiated, applanation of the cornea occurs. The suction cone 107 may then continue to move upward within position 304, which is represented as a shaded area rather than a line because any position in the z direction within that range is an acceptable position. Position 304 is known as the ideal work area where there is enough pressure on the eye 101 for applanation, but not so much pressure as to squeeze the eye. As the suction cone 107 continues to move upwards within the ideal work area position 304, the position of suction cone 107 in the z direction may be presented to the user in real time. If the suction cone 107 moves upwards in the z direction past the ideal work area position 304, there is a danger that too much pressure could squeeze the eye 101. Therefore, a threshold limit position 305, known as the z stop limit is defined within the z direction. A schematic representation of the suction cone 107 at this threshold position is shown in FIG. 3C. When the measuring device 201 measures that the suction cone 107 has reached this position 305, this is also presented, often in real time. The user or the system should halt all further upward movement in the z direction. System 200 may further prevent further upward movement in the z direction, particularly if processor 202 is connected to control device 108. Instead of stopping further upward movement only when the suction cone 107 has reached the z stop limit position 305, the system may also be configured to automatically hold suction cone 107 still in a defined position within the ideal work are 304.

Figure 4:
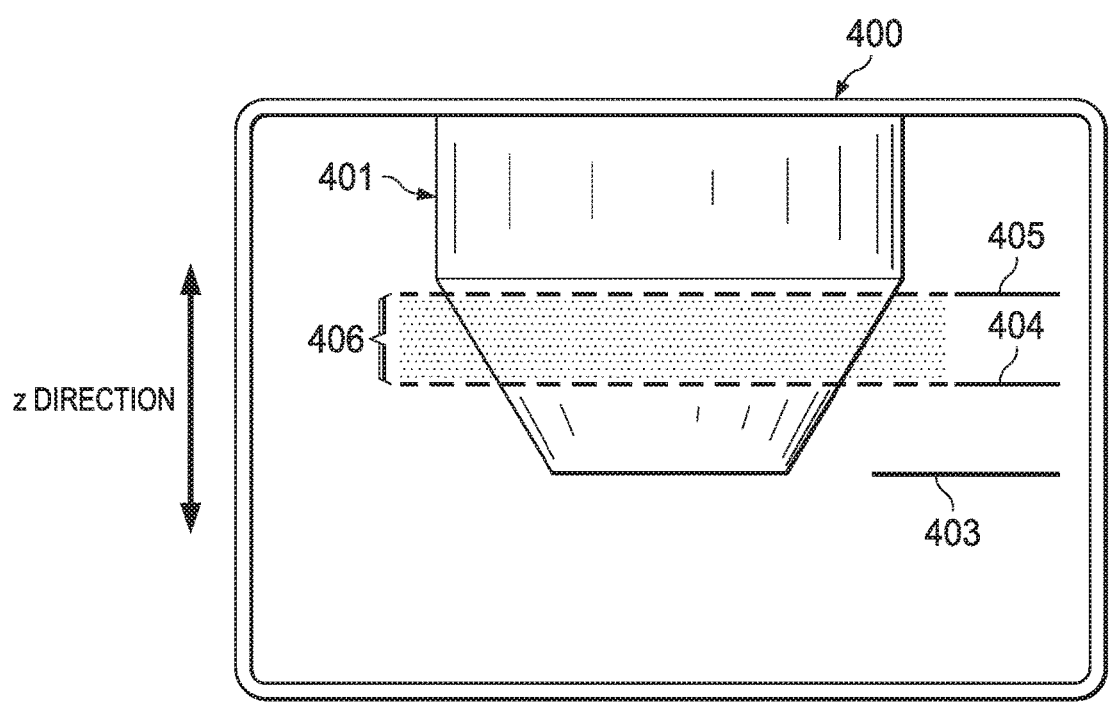
FIG. 4 is a pictorial representation showing threshold markers corresponding to the position of a suction cone during docking on an eye in femtosecond laser ophthalmic surgery.

FIG. 4 is an example screen display 400 of a pictorial representation showing the position of suction cone 107 during docking on an eye 101 in femtosecond laser ophthalmic surgery as depicted in FIG. 3. As shown, the screen display 400 provides a pictorial representation 401 of the suction cone 107 as well pictorial threshold markers 403 through 406 which correspond to threshold positions 302 through 305. As the suction cone 107 is moved up or down in the z direction during docking, the pictorial representation of the suction cone 401 will show when the actual suction cone 107 reaches the threshold positions via the corresponding pictorial threshold markers. When the suction cone 107 has reached a threshold position 302 of low contact with the eye 101, "EC Low," the display 400 will show the pictorial representation 401 with the suction cone at threshold marker 403. When the suction cone 107 has reached a threshold position 303 of high contact with the eye 101, "EC High," the display 400 will show the pictorial representation 401 of the suction cone at threshold marker 404. At this threshold position, the suction cone 107 has reached the ideal work area 304 and the second vacuum 106 will be initiated to provide suction for applanation of the cornea. While the suction cone 107 remains within the ideal work area 304, the display 400 will show the pictorial representation 401 of the suction cone within threshold marker 406. If the suction cone 107 has reached z stop limit threshold position 305, the display 400 will show the pictorial representation 401 of the suction cone at threshold marker 405. In addition, a warning indicator, such as a flashing light, a change in color of all or a component of the pictorial representation, or a text message on display 400 may occur.

Pictorial representation 401 may present more than one threshold marker 403-406 simultaneously. For instance, it may present all threshold markers 403-406 simultaneously as depicted in FIG. 4. However, pictorial representation 401 may also present only one threshold marker, such as the threshold marker closest to the measured position of the suction cone. Pictorial representation 401 may also present only a subset of threshold markers 403-406 simultaneously. For instance, it may present the threshold marker most recently passed and the next approaching threshold marker, or it may present the threshold marker closest to the measured position and another significant threshold marker, such as the threshold marker 405 corresponding to the z stop position. If all threshold markers are not displayed simultaneously, one or more of those that are displayed may change over time during the surgery as the suction cone moves in the z direction.

Figure 5:
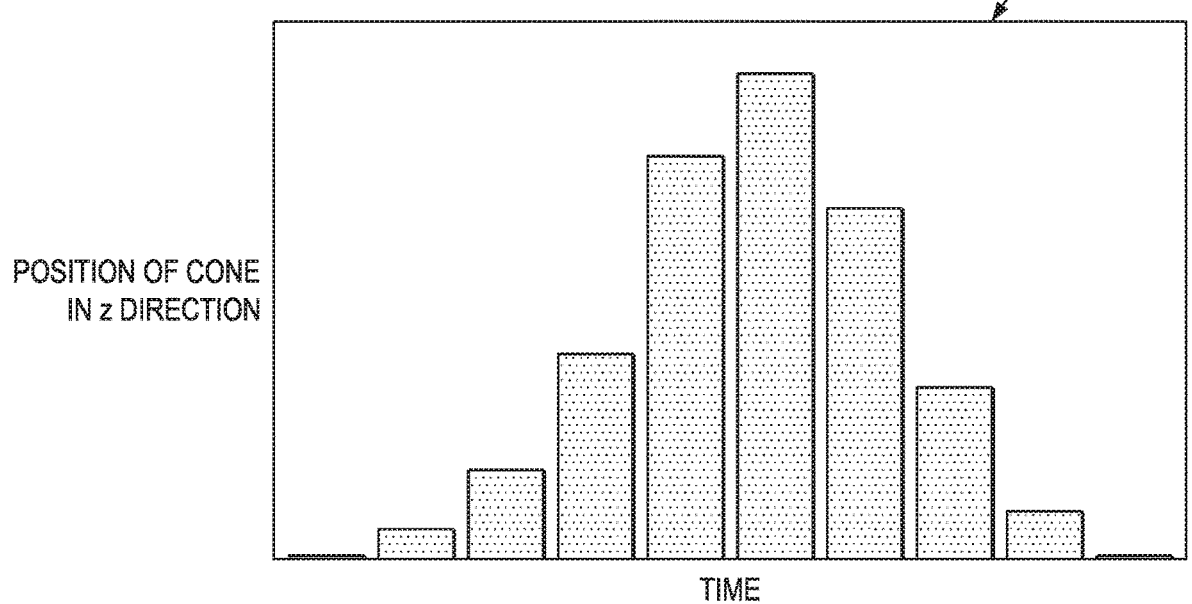
FIG. 5 is a histogram showing position of a suction cone in the z direction during docking on an eye in femtosecond laser ophthalmic surgery.

Measurements made with measuring device 201 may also be used to construct a histogram 500 showing the position of a suction cone in the z direction during docking on an eye in femtosecond laser ophthalmic surgery, such as that shown in FIG. 5. In order to construct such a histogram, the data relating to the measured position is recorded so that the histogram indicates suction cone 107's movement in the z direction over time. The histogram may be updated in real time or shown as a static histogram at the end of the treatment.

In addition to being used to present the position of the suction cone 107 in the z direction during docking on a cornea, the positions measured by measuring device 201 may also be used to determine the curved interface of the cornea during docking and initiation of and level of applanation of the cornea. This information may also be presented in real time.

Figure 6:
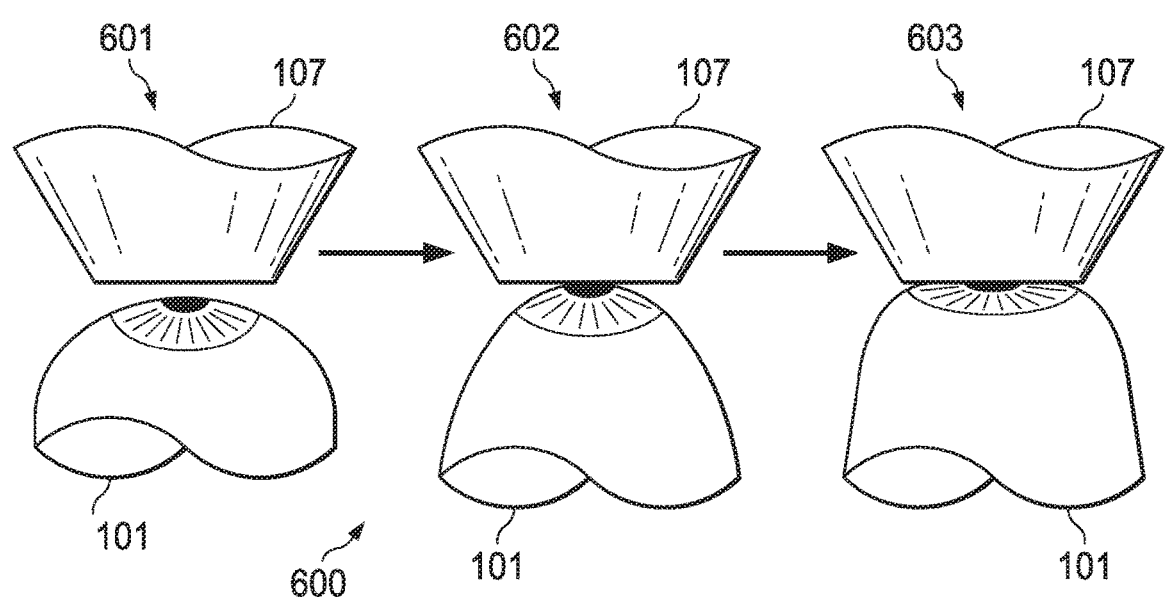
FIG. 6 is a pictorial representation of applanation including the changing shape of a cornea during docking on an eye in femtosecond laser ophthalmic surgery.

Referring now to FIG. 6, applanation 600 of a cornea during docking in femtosecond laser ophthalmic surgery is depicted. As shown, after initial contact with the patient's eye 101, as the suction cone 107 moves upwards in the z direction, the shape of the cornea changes as the suction cone moves upwards in the z direction and applies more pressure on the eye. When there is no eye contact with the suction cone 107, there is no corneal deformation and any pictorial representation will present the eye 101 with no corneal deformation 601. As the suction cone 107 is moved upwards with the eye 101, applanation is initiated when there is minimal corneal deformation 602, which may also be presented. When full applanation has occurred 603, and the cornea is sufficiently flat for femtosecond laser treatment to begin, this may also be presented. As an alternative to presenting a pictorial representation of applanation as depicted in FIG. 6, a display may instead present another indicator of the degree of applanation, such as an indicator of when applanation is initiated and an indicator of when full applanation has occurred.

Figure 7:
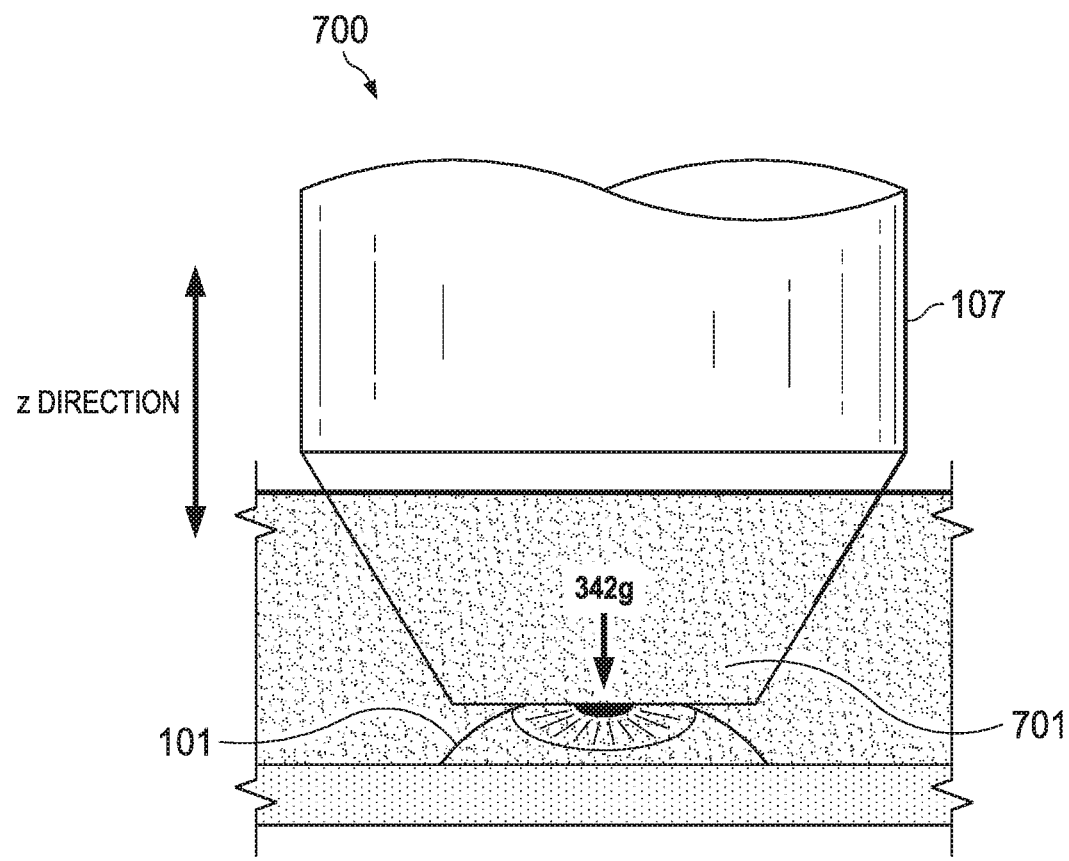
FIG. 7 is a pictorial representation of the load from a suction cone on an eye as a function of the position in the z direction of the suction cone during docking on the eye in femtosecond laser ophthalmic surgery.
Figure 8:
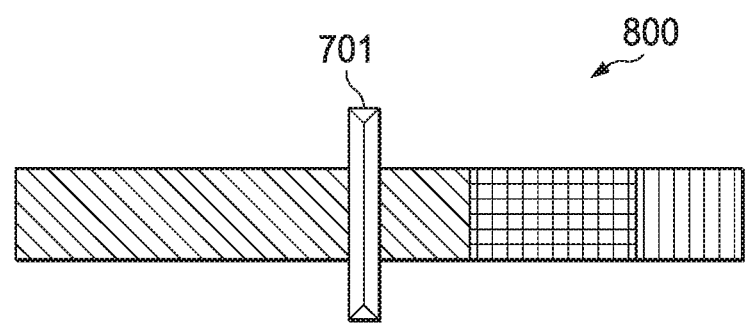
FIG. 8 is a bar graph showing the load from a suction cone on an eye as a function of the position in the z direction of the suction cone during docking on the eye in femtosecond laser ophthalmic surgery.

Suction cone 107 positions measured by measuring device 201 may also be used by processor 202 to calculate other information regarding the eye, which may be presented in a pictorial representation or a graph. For instance, the example display of FIG. 7 presents a pictorial representation 700 of the load resting on the eye 101 as a function of the z direction position of suction cone 107 during docking. In addition to presenting a pictorial representation of the position of the suction cone 107 in the z direction during docking, the positions measured by the measuring device 201 may also be used to determine the load amount 701 on eye 101 from the suction cone 107 resting on eye 101 at any given time, including in real time. This load may, for instance, be measured in grams or another load unit, or it may simply be depicted in relative amounts, for instance by color, as acceptable, approaching unacceptable, or unacceptable, or as a bar graph, such as that of FIG. 8. As shown in FIG. 7, after initial contact with the eye 101, as the suction cone 107 moves upwards in the z direction, the measurement of the z direction position of the suction cone 107 may be converted to a load amount 701.

Figure 9:
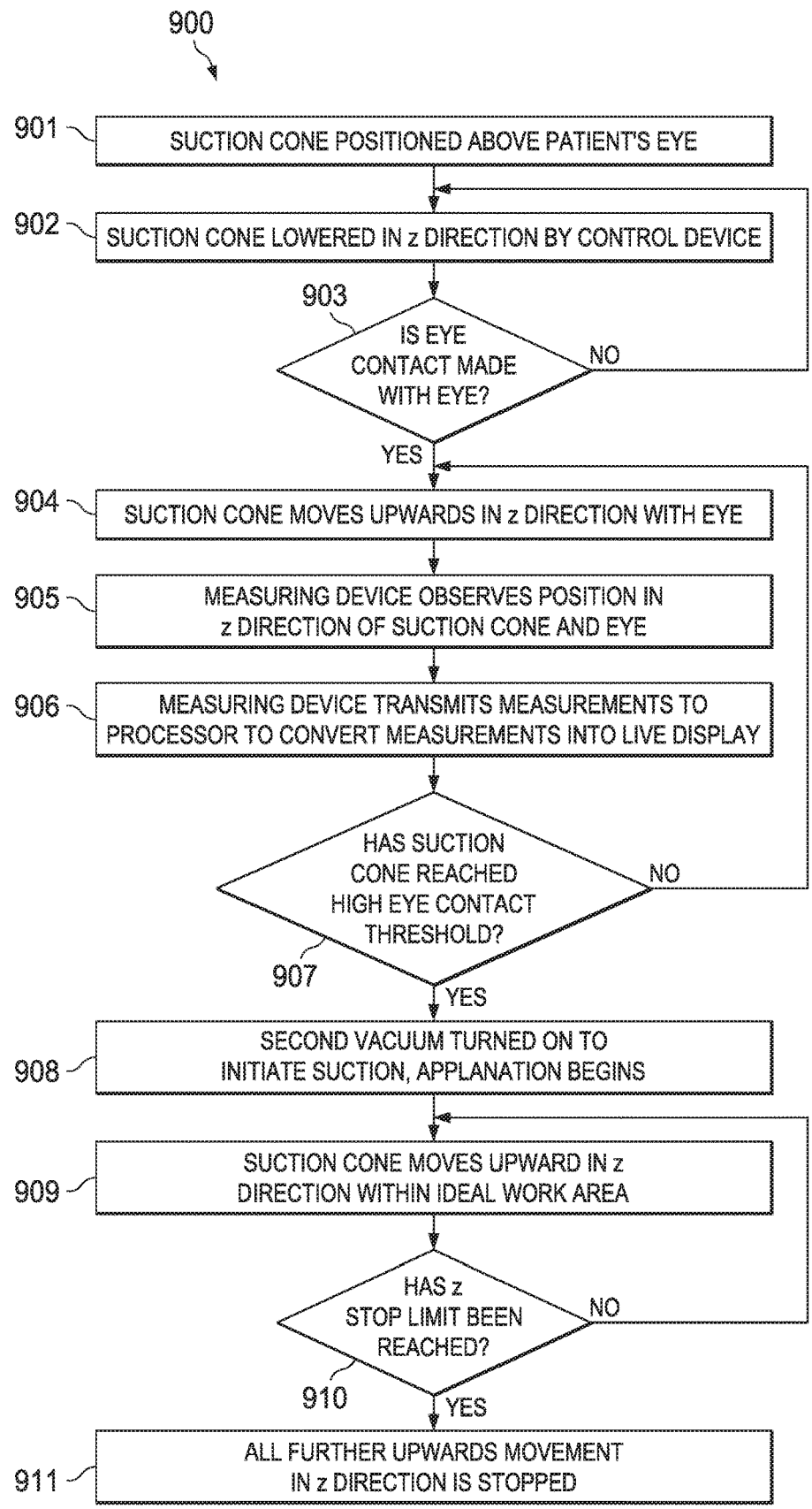
FIG. 9 is a flowchart of a method for docking on an eye in femtosecond laser ophthalmic surgery.

Referring now to FIG. 9, a method 900 for docking in femtosecond laser ophthalmic surgery, as described herein, is depicted as a flowchart. Method 900 may be used in conjunction with the systems and apparatus described above.

Method 900 may be used to ensure that a suction cone is within the ideal work area for femtosecond laser treatment. Certain operations described in method 900 may be optional or may be rearranged in variant femtosecond laser ophthalmic surgeries using the systems and apparatuses of this disclosure.

Method 900 may begin, at step 901, by positioning the suction cone above a patient's eye. At step 902, the suction cone is moved downwards in the z direction using a control device until it makes contact with the patient's eye.

At step 903, a measuring device measures the position of suction cone and presents information related to the position on a display, so that the user may detect if the suction cone has made contact with the patient's eye. If eye contact has been made, the method moves to step 904. If eye contact has not yet been made, step 902 is continued until eye contact is made.

Once eye contact has been made, at step 904, the suction cone along with the patient's eye are moved upwards in the z direction using the control device. At step 905, the measuring device measures the position of the suction cone in the z direction. At step 906, the measuring device transmits data relating to the measured positions to a processor, which uses the data to create a pictorial representation, histogram, or other graph based on the data, which are displayed on a display, optionally in real time. A pictorial representation may also present one or more threshold markers and show the position of the docking cone with respect to these threshold markers. The threshold markers may include a threshold marker corresponding to at least one of a low eye contact threshold position, a high eye contact threshold position, an ideal work area threshold position, and a z stop limit threshold position.

At step 907, if the suction cone has reached the high eye contact threshold position, suction is applied by a second vacuum to initiate applanation of the patient's cornea, step 908. If this level has not yet been reached, steps 904-906 are repeated until the high eye contact threshold point is reached. Once applanation is initiated, at step 909, the suction cone may be moved upwards in the z direction within the ideal work area until it reaches the z stop limit threshold position. At step 910, if the suction cone has reached the z stop limit threshold position, all further movement of the suction cone in the upwards z direction will be stopped, step 911.

In addition to measurements of the suction cone position, the measuring device may also measure the position of the eye, or of another reference point. Data relating to these positions may also be used to present a pictorial representations, histogram, or other graph based on the data.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A system for femtosecond laser ophthalmic surgery comprising: a suction cone; a control device configured to move the suction cone up and down in a z direction with respect to an eye; a measuring device configured to measure the position of the suction cone in the z direction with respect to the eye; a processor configured to process, the measured position of the suction cone in the z direction with respect to the eye to create a pictorial representation, based on the position of the suction cone in the z direction with respect to the eye; a display configured to receive the pictorial representation, when transmitted from the processor and to present the pictorial representation, during femtosecond laser ophthalmic surgery; and wherein the pictorial representation comprises a representation of the suction cone, a representation of a rest threshold position, a representation of a low contact threshold position, a representation of a high contact threshold position, a representation of an ideal work area threshold position, and a representation of a z stop limit threshold position, and wherein the representation of the suction cone is static while the representations of each of the rest threshold position, the high contact threshold position, the ideal work area threshold position, and the representation of a z stop limit threshold position move as the suction cone moves in the z direction with respect to the eye.

2. The system of claim 1, wherein the measuring device comprises a light barrier, a switch, a distance-measuring device, or a combination thereof.

3. The system of claim 1, wherein the display comprises a screen, a head-up display, or a combination thereof.

4. The system of claim 1, wherein the processor k configured to create and the display k configured to present the pictorial representation in real time.

5. The system of claim 1, wherein the processor is configured to process information data relating to the measured position to create at least two of a pictorial representation, based on the position of the suction cone in the z direction and the display is configured to display at least two of the pictorial representation simultaneously.

6. The system of claim 1, wherein the display presents a warning indicator when the suction cone reaches the z stop threshold position.

7. The system of claim 1, wherein the processor is further configured to determine when the suction cone reaches a z stop threshold position and to stop further upward movement of the suction cone in the z direction when the suction cone reaches the z stop threshold position.

8. The system of claim 1, wherein the processor is further configured to create and the display is further configured to present a pictorial representation of applanation of the eye.

9. The system of claim 1, wherein the system is further configured to record the measured positions of the suction cone over time and the processor is further configured to create and the display is further configured to present a histogram of the measured positions of the suction cone over time.

10. The system of claim 1, wherein the processor is further configured to create a pictorial representation, depicting a load resting on the eye as a function of the measured position of the suction cone.

11. A method of docking a suction cone in femtosecond laser ophthalmic surgery, the method comprising:
measuring the position of the suction cone in the z direction using a measuring device;
generating data relating to the measured position of the suction cone using the measuring device;
processing the data relating to the measured position of the suction cone with a processor to create a pictorial representation of the position of the suction cone in the z direction; and
transmitting the pictorial representation from the processor to a display that presents the pictorial representation;
wherein the position of the suction cone in the z direction may be measured at least one threshold position of the suction cone in the z direction, and, the at least one threshold position includes a rest threshold position, a low contact threshold position, a high contact threshold position, an ideal work area threshold position, and a z stop limit threshold position.

12. The method of claim 11, wherein the display presents a warning indicator when the suction cone reaches the z stop threshold position.

13. The method of claim 12, wherein upward movement of the suction cone in the z direction is stopped when the suction cone has reached the z stop threshold position.

14. The method of claim 11, wherein the suction cone changes position over time, the processor further processes data relating to the measured position of the suction cone over time to produce a histogram of the measured position of the suction cone over time, and the display displays the histogram.

15. The method of claim 11, wherein the processor uses data relating to the measured position of the suction cone to determine the load of the suction cone resting on the eye and to create a graph depicting this load, which is transmitted to and presented by the display.

* * * * *